United States Patent [19]

Strobridge

[11] 4,414,199
[45] Nov. 8, 1983

[54] TOOTHPASTE

[75] Inventor: John R. Strobridge, Comstock Park, Mich.

[73] Assignee: Amway Corporation, Ada, Mich.

[21] Appl. No.: 398,343

[22] Filed: Jul. 15, 1982

[51] Int. Cl.³ .......................... A61K 7/16; A61K 7/18
[52] U.S. Cl. .......................................... 424/52; 424/49
[58] Field of Search ................................... 424/49-58, 424/52

[56] References Cited

U.S. PATENT DOCUMENTS

| | | | |
|---|---|---|---|
| 1,275,275 | 8/1918 | Levinson | 424/49 |
| 3,105,013 | 9/1963 | Saul | 167/93 |
| 3,120,469 | 2/1964 | Tamas | 167/93 |
| 3,282,792 | 11/1966 | Fiscella | 167/93 |
| 3,839,213 | 10/1974 | Hill | 424/56 |
| 3,935,304 | 1/1976 | Januszewski et al. | 424/49 |
| 4,042,680 | 8/1977 | Muhler et al. | 424/55 |
| 4,108,979 | 8/1978 | Muhler et al. | 424/49 |
| 4,108,981 | 8/1978 | Muhler et al. | 424/52 |
| 4,122,163 | 10/1978 | Muhler et al. | 424/52 |
| 4,174,387 | 11/1979 | Cordon et al. | 424/52 |
| 4,209,504 | 6/1980 | Harth et al. | 424/49 |
| 4,248,860 | 2/1981 | Watson | 424/57 |
| 4,280,822 | 7/1981 | Wason | 51/308 |
| 4,308,252 | 12/1981 | Tomaich et al. | 424/52 |

FOREIGN PATENT DOCUMENTS

| | | |
|---|---|---|
| 1273859 | 9/1961 | France . |
| 980485 | 10/1965 | France . |
| 23-176091 | 4/1948 | Japan . |
| 49-24224 | 6/1974 | Japan . |

OTHER PUBLICATIONS

The Uses of Colloidal Kaolins, Jar. Hojka. Ceskoslov. Mydlar Vonavkar Chemical Abstract, vol. 33 of 1959, p. 7959, Abstracts 187.
Abrasive Properties of Some Domestic Toothpastes and Powders. Koren, V. N.; Fedorov, Chemical Abstract, vol. 69 of 1968, p. 9322/Yu.A., Abstracts 99376m.
Colloidal Kaolin in Soaps and Cosmetics. John Glenn. Chemical Abstract, vol. 33 of 1939, p. 2748.
Aluminum Compounds in Fluorinated Toothpastes and Dental-Prophylaxis Pastes. Chemical Abstract, vol. 59 of 1963, p. 7315/Yugve Ericsson.
Author: Putt et al. Journal Dental Research, vol. 54 of 1975, pp. 527 to 534.
Studies of Prophylaxis Pastes Containing Sodium-Potassium Aluminum Silicate and Fluoride Journal Dental Research, Jul. of 1979, 58(7) 1659–1663, Putt et al.
Fluoride Prophylaxis Pastes, Journal Dental Research, Jul. 1979, pp. 1660–1663, vol. 58, No. 7, Putt et al.
Dental Factice. Nao Sakurai Pharmaceuticals, Cosmetics, Perfumes, (1951) 4894.
Dentifrices, Henri Dumontier Essential Oils and Cosmetics, 15622.
Chemical Abstract, vol. 33 of 1959, p. 7959.
Chemical Abstract, vol. 69 of 1968, p. 9322.
Chemical Abstract, vol. 33 of 1939, p. 2748.
Chemical Abstract, vol. 59 of 1963, p. 7315.
Journal Dental Research, vol. 54 of 1975, pp. 527 to 534.
Journal Dental Research, Jul. of 1979.

*Primary Examiner*—Shep K. Rose
*Attorney, Agent, or Firm*—Price, Heneveld, Huizenga & Cooper

[57] ABSTRACT

The specification discloses a fluoride toothpaste using a calcined kaolin abrasive which is at least 80% calcined and which has a particle-size distribution such that the majority of particles are between 1 and 10 microns in diameter, and not more than 35% of the particles are under one micron in diameter. The resulting toothpaste shows surprising efficacy in terms of fluoride availability, fluoride uptake on human enamel, enamel solubility reduction and polishing and stain removal.

20 Claims, 1 Drawing Figure

TOOTHPASTE

BACKGROUND OF THE INVENTION

The present invention relates to fluoride toothpastes using kaolin as the abrasive ingredient. Kaolin is known to be a desirable abrasive for toothpastes because it is inexpensive and because it does clean and polish effectively.

U.S. Pat. No. 4,122,163 discloses a fluoride toothpaste using calcined kaolin as the abrasive. The kaolin used is said to be predominently of the gamma alumina or mullite form. As kaolin is calcined, it undergoes a fairly sharp endothermic reaction at about 520° C., where the kaolin converts to the gamma alumina crystal form. As heating continues, the kaolin undergoes an exothermic reaction at from about 975° to about 990° C. where the crystal form changes from the gamma alumina form to the mullite form.

While the gamma alumina/mullite kaolin employed by Muhler is of a very high degree of purity, having a whiteness index of not more than 10 and a brightness of at least about 93.0, I have found that this kaolin still exerts a detrimental affect on fluoride availability as the toothpaste ages.[1] This is surprising because of the high degree of purity of the kaolin. One would expect an adverse impact on fluoride availability due to impurities in the kaolin. However the Muhler patent does not explain why fluoride availability decreases fairly dramatically with aging when the gamma alumina/mullite kaolin is used.

[1] Fluoride availability refers to the availability of soluble fluoride ion in the toothpaste composition. To the extent that the fluoride reacts or complexes with other ingredients in the toothpaste, it becomes effectively unavailable for the purpose for which it is intended, i.e., to be taken up by the enamel of the teeth.

While other prior art patents have suggested the use of kaolin as an abrasive in fluoride toothpastes, no such fluoride toothpastes have ever been commercialized, to the best of my knowledge. Prior artisans have heretofore failed to realize the criticality of the combination of factors which I have found necessary in order to make a suitable fluoride toothpaste utilizing a kaolin abrasive.

SUMMARY OF THE INVENTION

The present invention comprises a fluoride toothpaste utilizing a calcined kaolin abrasive wherein the calcined kaolin is at least 80% calcined to the mullite crystal form. The kaolin must also have a particle size distribution such that the majority of the particles are sufficiently fine to afford good polishing without abrasion, but such that less than about 35% of its particles are under 1 micron in diameter.

The resulting fluoride toothpaste shows not only a high degree of fluoride availability when the product is first formulated, but also shows a significant resistance to degradation of fluoride availability with aging. This product also yields significantly superior polishing results. Perhaps most surprisingly, this product shows significantly superior in vitro fluoride uptake by human enamel.

These and other aspects, features and advantages of the invention will be more fully understood and appreciated by reference to the written specification and appended drawing.

DESCRIPTION OF THE PREFERRED EMBODIMENT

Figure 1:
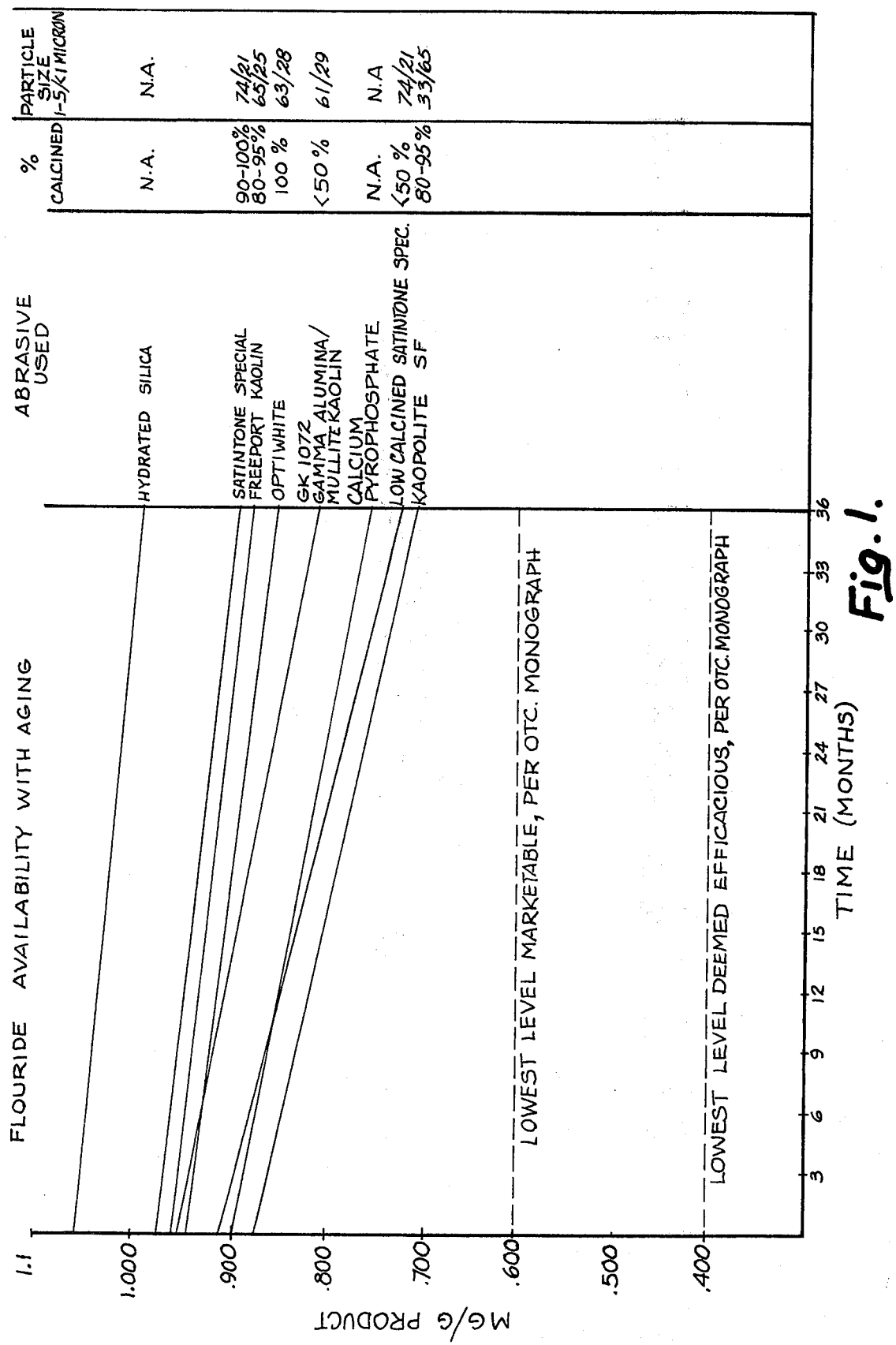
FIG. 1 is a graph showing available fluoride in various toothpastes with aging.

In the preferred embodiment, the kaolin used in the fluoride toothpaste of the present invention is at least 80%, and most preferably at least 90%, calcined to the mullite crystalline form. It has a particle size distribution such that more than 50% of the particles lie between 1 to 10 microns, and preferably between 1 to 5 microns, and such that less than 5% exceed 10 microns and less than 35% are less than 1 micron in diameter.

The basic formula for the toothpaste comprises from 5 to 70% of such kaolin, from 0.05 to 1% fluoride ion,[2] 5 to 70% humectant and from 0.5 to 10% binder. Other desirable ingredients include from 0.5 to 5% surfactant, flavoring ingredients, 0.05 to 10% titanium dioxide whitener, sequestering agents and preservatives. All percentages are by weight.

[2] Actually, 0.1% fluoride ion is the maximum allowed by the F.D.A. in an over-the-counter fluoride toothpaste.

Throughout this patent, the degree of calcination is referred to in terms of percent conversion to the mullite crystal form. I wish to make it clear, however, that I am making reference to this crystal form as a convenient way of expressing the manner in which I determined whether a particular kaolin would be acceptable or not. I did not specifically make a crystal structure study to confirm that 80% of the particles had a particular crystal instructure. More specifically, I evaluated each kaolin by conducting a differential thermal analysis of the kaolin. If one takes uncalcined kaolin and gradually increases its temperature pursuant to differential thermal analysis, one will find that at about 975° to 990° C., an exothermic reaction occurs which gives off a significant amount of heat resulting in a peak on the analysis graph. It is my understanding that this reaction is a result of the change in the crystalline form from the gamma alumina form to the mullite form. Hence it is concluded from differential thermal analysis that if a particular kaolin yielded a peak at 975° to 990° C. which was only 20% of the peak resulting from a differential thermal analysis of an uncalcined kaolin, then the calcined kaolin being tested is at least 80% mullite crystal in form.

Similarly in discussing the gamma alumina crystal form, I did not do a specific crystal structure analysis. Rather it is my understanding that the significant endothermic reaction peak which occurs at about 520° C. in a differential thermal analysis of uncalcined kaolin reflects the point at which the kaolin is converted to the gamma alumina crystal form.

The importance of having the proper combination of degree of calcination and particle size distribution can be seen by reference to Table I, Table II and FIG. 1. Six fluoride toothpaste test formulations, all identical except for the particular kaolin used, and two commercially available toothpastes using the abrasives indicated were tested for fluoride availability initially and after one month intervals of accelerated aging. In each test formula, one milligram of theoretically available fluoride ion was provided for each gram of product. It is known that this is also the level of theoretically available fluoride in the two commercially available toothpastes based on hydrated silica and calcium pyrophosphate respectively, because this is the maximum theoretically available fluoride which is allowed in an over-the-counter product. An initial fluoride availability of 0.96 means that instead of 1 milligram per gram of product, only 0.96 milligrams of fluoride ion was actually available in water soluble, ionized form. The initial fluoride availability of 1.065 for the commercially available hydrated silica fluoride toothpaste is the result of allowable variations from the maximum level of 1 milligram per gram.

Accelerated aging is achieved by storing the toothpaste at 40° C. It is generally accepted in the industry that one month of accelerated aging at 40° C. is equivalent to eight months of ambient aging. Thus in converting the information contained in Table I to graph form in FIG. 1, the points were placed at 8 months, 16 months and 24 months respectively on the time abscissa. A point was also placed at 36 months, based on the average slope determined from the first four points, i.e., the initial determination and the determination at the end of months one, two and three of accelerated aging. Table I also discloses an accelerated aging test performed for one month at 50° C., which is 10° in excess of the industry accepted standard. The results of this one month determination were not plotted on the FIG. 1 graph, but they are in accordance with the trends indicated on that graph.

The degree of calcination is expressed as a percentage of conversion to the mullite crystal form. That figure is not applicable with respect to the commercially available hydrated silica and calcium pyrophosphate formulas, and this is indicated both in Table I and FIG. 1. Particle size distributions for the kaolin are shown in Table II in total, and in abbreviated form in Table I and FIG. 1.

TABLE I

FLUORIDE AVAILABILITY INITIALLY AND WITH AGING

| Abrasive | % Calcination | Particle Size 1-5/<1 mic | Initial Fluoride | Accelerated 1 mo | 2 mo | 3 mo | 1 mont (50° C.) |
|---|---|---|---|---|---|---|---|
| Hydrated Silica | N.A. | N.A. | 1.065 | 1.04 | 1.055 | 0.995 | 1.02 |
| Satintone Special | 90-100 | 74/21 | 0.965 | 0.96 | 0.94 | 0.92 | 0.97 |
| Freeport Kaolin | 80-95 | 65/25 | 0.96 | 0.94 | 0.89 | 0.92 | 0.935 |
| Optiwhite | 100 | 63/28 | 0.945 | 0.915 | 0.875 | 0.895 | 0.89 |
| Georgia Kaolin 1072 | <50% | 61/29 | 0.975 | 0.875 | 0.895 | 0.865 | 0.895 |
| Calcium pyrophosphate | N.A. | N.A. | 0.90 | 0.87 | 0.805 | 0.82 | 0.865 |
| Low Calcined Sat. Sp. | <50% | 74/21 | 0.915 | 0.87 | 0.80 | 0.80 | 0.79 |
| Kaopolite SF | 80-95 | 33/65 | 0.875 | 0.84 | 0.765 | 0.78 | 0.83 |

The kaolins are all indicated by their trademark where appropriate. It will be noted that the three formulas using kaolins which are more than 80% calcined to the mullite crystal form, show a remarkably similar and limited degree of deterioration of fluoride availability with time. These would be the formulas employing Satintone Special ™ from Engelhard Minerals, Al-Silate-O ™ kaolin from Freeport (listed as Freeport kaolin) and Optiwhite ™ from Burgess Pigments.

In contrast, the formulation using Kaolin GK1072 ™ from Georgia kaolin dropped off significantly more sharply than the other three. GK1072 ™ is a gamma alumina/mullite kaolin which was acquired from Indiana University and which according to Indiana University personnel was used by Joseph C. Muhler in connection with the work which led to the issuance of U.S. Pat. No. 4,122,163. This kaolin is less than 50% calcined to the mullite crystalline form.

In order to confirm that the low degree of calcination was responsible for the more rapid degree of deterioration in fluoride availability of this kaolin, I also obtained a sample of Satintone Special ™ specifically before it was calcined to the normal extent, (i.e., such that from 90 to 100% has been converted to the mullite crystalline form). This low calcined Satintone Special ™ was calcined to less than 50% mullite. The degree of deterioration of fluoride availability is almost parallel to the degree of deterioration for GK1072. ™

The Table I, FIG. 1 results for the Kaopolite SF ™ (the abrasive used in prior U.S. Pat. Nos. 3,105,013 and 3,282,792) formula illustrate the importance of combining proper particle size distribution and degree of calcination. Kaopolite SF ™ has the requisite degree of calcination for the broader aspects of this invention. However as can be seen by reference to Table II, the particle size distribution for Kaopolite SF ™ is strikingly different from that for the other acceptably calcined kaolins, the Satintone Special, ™ Freeport Kaolin ™ and Optiwhite. ™ Specifically, the former has 65% of its particles at less than 1 micron, while the latter three are all at less than 35% below the 1 micron level. Similarly, the former has only 33% of its particles at from 1-5 microns while the latter three are well in excess of 50% in that range. As a result, Kaopolite SF ™ also exhibited a high degree of degradation of fluoride availability in spite of its 80%-95% calcination. The slope of the Kaopolite SF ™ line is approximately parallel to the slope of the GK1072 ™ and low calcined Satintone Special ™ lines.

TABLE II

| Particle Size Range (mic) | Engelhard Sat. Spec. | Freeport Kaolin | Burgess Optiwhite GK1072 | Low Calcined Sat. Sp. | Kaopolite SF |
|---|---|---|---|---|---|
| 50.0-10.0 | 1% | 2% | 2% | 3% | 1% | 1% |
| 10.0-5.0 | 5% | 8% | 7% | 7% | 5% | 1% |
| 5.0-1.0 | 74% | 65% | 63% | 61% | 74% | 33% |
| <1.0 | 21% | 25% | 28% | 29% | 21% | 65% |
| % Calcination | 90-100% | 80-95% | 100% | less than 50% | less than 50% | 80-95% |

Particle size is also important to polishing efficacy. It is well-known that larger sized particles, for example those in excess of about 10 microns, must be avoided in order to avoid excessive abrasion of the teeth. Finer particles are known to afford better polishing results without abrasion. Muhler U.S. Pat. No. 4,122,163 emphasizes that the particles must be predominently less than about 10 microns in diameter, with a major portion being even less than 2 microns in diameter. Japanese Pat. No. 24,224 of 1974 emphasizes that all of the kaolin particles should be less than 1 micron in diameter.

As noted above, however, I have found that these patents fail to recognize the adverse impact of ultra fine kaolin particles on fluoride availability, especially with aging. I have found that less than 35% of the particles should be under 1 micron in diameter, and preferably less than 30% of the kaolin particles should be under 1 micron. The majority of the particles, i.e., more than 50%, should fall between 1 and 10 microns, and preferably between 1 and 5 microns. Most preferably, no more than 5% of the particles should be greater than 10 microns and no more than 10% should be within the range of from 5 to 10 microns.

I have also discovered that if there are excessive amounts of particles under 1 micron, the product rheology is adversely affected. It becomes too stringy. This is undesirable both from the aesthetic viewpoint of the product user, and from a processing standpoint. The stringiness impedes processing of the product during manufacture.

I discovered the adverse impact of ultra fine particles on rheology first. My subsequent discovery of the adverse impact of particle size on fluoride availability was entirely serendipitous and unexpected.

While the fluoride toothpaste based on hydrated silica shows a high degree of fluoride availability even with aging, in vitro fluoride uptake tests on human enamel reveal that the toothpaste made in accordance with the present invention is surprisingly superior to the hydrated silica toothpaste formulation. Significantly more fluoride is actually absorbed by human enamel brushed with the toothpaste of the present invention than with the toothpaste incorporating the hydrated silica.

Basically, the fluoride uptake test involves isolating standard enamel surfaces on human incisors (4 mil. disks, round, flat). After dentifrice application and rinsing, one layer of enamel is removed (etched) with perchloric acid (1 mil. of acid for 30 seconds). The solution is then diluted 1 to 1 with a buffer and analyzed for fluoride. A second layer is then removed using a 60 second etch and the solution analyzed in the same manner. This is in accordance with OTC Panel Method No. 40. More specifically, the evaluation for each sample of toothpaste analyzed was conducted as follows:

1. Four mm diameter enamel cylinders were excised from cleaned human incisors. The outer layer was removed by 2 M perchloric acid. The enamel was mounted and sealed with blue inlay casting wax. It was then ground flat with 600 grit silicon paper.

2. Each enamel piece was rotated in 2 M perchloric acid to remove 2 layers. One ml of acid was used for 30 seconds to obtain the first background layer, and then another one ml for 60 seconds to obtain the second. These solutions were analyzed for fluoride by diluting them 1:1 with alkaline Orion TISAB buffer. To obtain fluoride levels for the background enamel fluoride that are readable with the Orion Specific Ion Meter, the alkaline TISAB buffer used for dilution and buffering the perchloric acid etch solution s is 0.2 ppm fluoride. This fluoride amount is subtracted out before data is used. Fluoride values were determined with an Orion Fluoride electrode.

3. Then enamels were reground and decalcified for 24 hours with 0.025 M pH 4.5 lactate buffer modified with 0.0002 M disodium dihydrogen ethylidenehydroxydiphosphonate. (The methanehydroxydiphosphonate is not available).

4. Next each mounted enamel was rotated in supernatant from a 25% dentifrice slurry which was centrifuged for 30 minutes at 11,000 rpm.

5. After rinsing, 2 layers of enamel were removed with 2 M perchloric acid in the same manner as the pretreatment layers were.

6. These enamel solutions were diluted 1:1 with alkaline TISAB buffer and fluoride ion read with a fluoride electrode, as above.

7. After the background was subtracted, fluoride was reported as nanograms per enamel layer.

A fluoride toothpaste made in accordance with our most preferred formulation set forth hereinafter and using a calcined kaolin in accordance with the present invention was tested against two commercially available toothpastes, specifically the ones using hydrated silica and calcium pyrophosphate respectively as abrasives which were tested in the fluoride availability tests reported in Table I and FIG. 1. The results were as follows:

TABLE III

| | First Layer | Second Layer | Both Layers |
|---|---|---|---|
| Kaolin Toothpaste Fluoride | 1760 ± 204 | 131 ± 24 | 1900 ± 187 |
| Hydrated Silica Fluoride | 530 ± 75 | 168 ± 43 | 700 ± 32 |
| Calcium Pyrophosphate Fluoride | 785 ± 89 | 90 ± 42 | 875 ± 88 |

All values are in nanograms of fluoride per layer ±standard deviation.

As can be seen, a toothpaste made in accordance with the present invention shows significantly higher fluoride uptake than the two other commercially available fluoride toothpastes. Yet all have the OTC maximum theoretically available fluoride of 1 milligram per gram of product. While the superiority of a toothpaste made in accordance with the present invention to commercially available calcium pyrophosphate fluoride toothpaste would seem predictable in view of the fluoride availability tests of FIG. 1, it is surprising and unexpected in view of the FIG. 1 results that the fluoride toothpaste of the present invention is also significantly superior in fluoride uptake on human enamel than is the commercially available hydrated silica toothpaste since the latter shows a greater level of available fluoride over the period of the aging tests.

The extent to which the toothpaste of the present invention reduces enamel solubility was also compared to the two commercially available toothpastes discussed above. The test procedure is based on OTC Method No. 33 and is as follows:

1. Tooth crowns of molars, cuspids and bicuspids were cleaned by polishing with pumice flour. Most of the root areas were removed. The crowns were mounted in epoxy cement, F-88, six to a beaker, and sealed with blue inlay casting wax. Four sets of 6 crowns were used to test each dentifrice. Deprotection was accomplished at the beginning and between tests by 2 hours in 0.1 M pH 4.5 lactate buffer. This solution and all others were stirred at a speed close to 1725 rpm which is the speed for stirring as designated in OTC procedure #33.

2. Tests were carried out by determining the solution of the enamel in the buffer before and after the dentifrice treatment. The 0.1 M pH 4.5 lactate buffer was added to the beaker containing the 6 enamel crowns and stirred for 15 minutes at 37° C. The lactate was then removed and kept for the phosphate analysis. The crowns were rinsed 3 times at least.

3. Fifteen grams of dentifrice were mixed with 45 grams or ml of water and centrifuged. The supernatant was poured over the crowns and stirred for 5 minutes. Then the supernatant was discarded and the crowns rinsed well.

4. Again the lactate buffer was used on the crowns for 15 minutes, the same as before, in order to determine the solubility of the enamel after the treatment.

5. The solution of lactate, pre- and post-treatment, were analyzed for phosphate by the Fiske and Suba-Row established phosphate method.

6. The percent reduction in enamel solubility was calculated by subtracting the post-phosphate from the prephosphate, dividing by the prephosphate value and then multiplying by 100. The average results for the three toothpastes were as follows:

TABLE IV

| TOOTHPASTE | % REDUCTION IN ENAMEL SOLUBILITY |
|---|---|
| Kaolin fluoride toothpaste in accordance with the most preferred formula of the present invention. | 36.5% |
| Hydrated silica fluoride toothpaste. | 20% |
| Calcium pyrophosphate fluoride toothpaste. | 28% |

Thus in terms of reducing the solubility of tooth enamel, the kaolin fluoride toothpaste of the present invention is also significantly superior to commercially available fluoride toothpastes using other abrasives.

The toothpaste of the present invention is also superior to these commercially available toothpastes in polishing and stain removal results. Excised human teeth (24 per treatment) were dulled with hydrochloric acid and initial reflectance measurements were made via spectroradiometry techniques. The teeth were brushed in a brushing machine with the various toothpastes and reflectance measurements and spectro-radiometric measurements were made (before and after) to determine the level of polishing, as indicated by a change in photon radiance, and the level of stain removal as determined by spectro-radiometric comparison. Perceivable color changes to the eye are also indicated pursuant to a mathematical index. These tests are in accordance with industry accepted standards.

Two different toothpastes made in accordance with the present invention were tested, both being made in accordance with the most preferred embodiment formula set forth hereinafter. The difference between the two is that one uses the most preferred calcined kaolin, Satintone Special ™, while the other used a calcined kaolin which is in accordance with the broader aspects of the present invention, but which has a larger average particle size, specifically with 10% of its particles falling within the range of from 5 to 10 microns and 3.5% of its particles falling within the range of from 10 to 50 microns.

The results are reported in Table V below:

TABLE V

| | A | B | C | D |
|---|---|---|---|---|
| 1. Polishing (photon radiance) Treatment Mean Photon Radiance | 129.9 | 136.4 | 140.3 | 143.5 |
| 2. Stain Removal (% stain removal) Treatment Mean Stain Removal | 7.1 | 8.3 | 13.2 | 14.2 |
| 3. Perceivable Color Change Treatment | 40.9 | 48.6 | 80.1 | 83.3 |

Treatments:
A - Hydrated silica fluoride toothpaste.
B - Calcium pyrophosphate fluoride toothpaste.
C - Kaolin fluoride toothpaste, with slightly larger kaolin particles.
D - Most preferred Satintone Special ™ kaolin fluoride toothpaste.

The most preferred fluoride toothpaste made in accordance with the present invention has the following formula, with approximate ranges indicated in a second column:

MOST PREFERRED FLUORIDE TOOTHPASTE

| | % W/W | Range % |
|---|---|---|
| At least 80% calcined kaolin with less than 35% particles under one micron (most preferably Satintone Special ™) | 37.0000 | 5.0–70.0 |
| Deionized Water | 24.0006 | q.s. |
| Glycerine | 14.0000 | 5.0–70.0 |
| Sorbitol | 17.5000 | 5.0–70.0 |
| Titanium Dioxide | 2.0000 | 0.05–10.0 |
| Carboxymethyl Cellulose | 1.3500 | 0.50–5.0 |
| Sodium Lauryl Sulfate | 1.5000 | 0.50–5.0 |
| Flavoring Agent | 0.8500 | 0.05–5.0 |
| Magnesium Aluminum Silicate | 0.6230 | 0.05–5.0 |
| Sodium Saccharin | 0.3000 | 0.05–5.0 |
| Sodium Citrate | 0.2500 | 0.05–5.0 |
| Sodium Phosphate | 0.2000 | 0.05–5.0 |
| Methyl Paraben | 0.1500 | 0.01–5.0 |
| Propyl Paraben | 0.0500 | 0.005–5.0 |
| Coloring Agent | 0.0020 | 0.00001–2.00 |
| Sodium Fluoride | 0.2244 | 0.05–1.0 (.02–.5% F-) |

The glycerine and sorbitol used in the most preferred formula act as humectants, and also serve as sweeteners. Titanium dioxide is employed to give the toothpaste a bright white appearance. Carboxymethyl cellulose and magnesium aluminum silicate are both binders. Sodium lauryl sulfate is added as a surfactant. Sodium saccharin is the primary sweetener. Sodium citrate is added as a sequestering agent to tie up any free trivalent ions, as for example aluminum ions, in the formula. These trivalent ions would otherwise combine with the carboxymethyl cellulose binder to create a rubbery gel.

Sodium phosphate is added as a pH buffer. Methyl paraben and propyl paraben are both preservatives. Any of a variety of flavoring and coloring agents can be used.

The level of sodium fluoride, 0.2244% is the maximum allowed by the FDA in an over-the-counter fluoride toothpaste. This translates to 0.1% fluoride ion, with a little excess being allowed as an anticipated normal deviation. The range percent for the sodium fluoride, from 0.05% to 1%, translates to a maximum fluoride ion of about 0.5% (0.446), well in excess of the maximum allowed in a commercial O.T.C. product.

Naturally, the kaolin used must be of a relatively pure grade. It is well-known that excessive impurities in any abrasive can inhibit fluoride availability. Hence, all of the kaolins tested and reported above were of comparable, high degrees of purity. Whiteness and brightness are often measures of purity, and we have found it desirable that the kaolin have a brightness of at least about 89 and a whiteness index of at least about 13 or below.

Naturally the above is merely preferred embodiment of the invention and various changes and alterations can be made without departing from the spirit and broader aspects thereof as set forth in the appended claims.

The embodiments of the invention in which an exclusive property or privilege is claimed are defined as follows:

1. In a toothpaste containing fluoride and calcined kaolin, the improvement comprising:
   the calcined kaolin being at least 80% calcined to the mullite crystal form, the majority of the particles being sufficiently fine to afford good polishing without excess abrasion, but no more than about 35% of the particles being less than 1 micron in diameter.

2. The fluoride toothpaste of claim 1 wherein the particle size distribution of the calcined kaolin is such that more than 50% of the particles lie between 1 to 10 microns and less than 5% exceed 10 microns.

3. The fluoride toothpaste of claim 2 wherein more than 50% of the particles are from 1 to 5 microns and less than 10% are from 5 to 10 microns.

4. The fluoride toothpaste of claim 3 wherein less than 1% of the particles are from 10 to 50 microns, less than 5% of the particles are from 10 to 5 microns, at least 70% of the particles are from 1 to 5 microns, and no more than 30% of the particles are less than 1 micron in diameter.

5. The fluoride toothpaste of claims 1, 2, 3 or 4 wherein at least 90% of the kaolin is calcined to the mullite crystalline form.

6. The fluoride toothpaste of claim 5 wherein the active fluoride ingredient used is sodium fluoride.

7. The fluoride toothpaste of claim 6 which includes a titanium dioxide whitener.

8. The fluoride toothpaste of claims 1, 2, 3 or 4 wherein the active fluoride ingredient used is sodium fluoride.

9. A toothpaste comprising from 5 to about 70% of a calcined kaolin being at least 80% calcined to the mullite crystal form, and having the majority of its particles sufficiently fine to afford good polishing without excessive abrasion, but with no more than about 35% of its particles being under 1 micron in diameter;
   from about 0.02 to about 0.5% water soluble fluoride ion;
   from about 5 to about 70% humectant; and
   from about 0.5 to about 10% binder.

10. The fluoride toothpaste of claim 9 which additionally comprises from about 0.5 to about 5% surfactant.

11. The fluoride toothpaste of claim 10 which comprises from about 0.05 to about 10% titanium dioxide whitener.

12. The fluoride toothpaste of claim 10 which comprises from about 35 to about 40% of said calcined kaolin;
   from about 30 to about 40% of said humectant;
   from about 1 to about 3% of said binder; and
   from about 1 to about 2% of said surfactant.

13. The fluoride toothpaste of claim 9 which comprises from about 34 to about 40% of said calcined kaolin.

14. The fluoride toothpaste on any of claims 9, 10, 11, 12 or 13 wherein the particle size distribution of the calcined kaolin is such that more than 50% of the particles lie between 1 to 10 microns and less than 5% exceed 10 microns.

15. The fluoride toothpaste of claim 14 wherein more than 50% of the particles are from 1 to 5 microns and less than 10% are from 5 to 10 microns.

16. The fluoride toothpaste of claim 15 wherein less than 1% of the particles are from 10 to 50 microns, less than 5% of the particles are from 10 to 5 microns, at least 70% of the particles are from 1 to 5 microns, and no more than 30% of the particles are less than 1 micron in diameter.

17. The fluoride toothpaste of claim 16 wherein at least 90% of the kaolin is calcined to the mullite crystalline form.

18. The fluoride toothpaste of claim 15 wherein at least 90% of the kaolin is calcined to the mullite crystalline form.

19. The fluoride toothpaste of claim 14 wherein at least 90% of the kaolin is calcined to the mullite crystalline form.

20. The fluoride toothpaste of any claims 9 through 13 wherein at least 90% of the kaolin is calcined to the mullite crystalline form.

* * * * *